United States Patent [19]
Fogel

[11] Patent Number: 6,057,373
[45] Date of Patent: *May 2, 2000

[54] METHODS OF TREATING TARDIVE DYSKINESIA AND OTHER MOVEMENT DISORDERS USING NMDA RECEPTOR ANTAGONISTS

[75] Inventor: Barry S. Fogel, Waban, Mass.

[73] Assignee: Synchroneuron, LLC, Waban, Mass.

[*] Notice: This patent is subject to a terminal disclaimer.

[21] Appl. No.: 09/224,829

[22] Filed: Jan. 4, 1999

Related U.S. Application Data

[63] Continuation-in-part of application No. 08/861,801, May 22, 1997, Pat. No. 5,866,585.

[51] Int. Cl.⁷ .................................................. A61K 31/04
[52] U.S. Cl. ............................................................. 514/740
[58] Field of Search ................................ 514/6, 742, 724, 514/8, 289, 662, 775, 740

[56] References Cited

U.S. PATENT DOCUMENTS

| | | |
|---|---|---|
| 4,122,193 | 10/1978 | Scherm et al. |
| 4,233,229 | 11/1980 | Chakrabarti . |
| 4,355,043 | 10/1982 | Durlach . |
| 5,061,703 | 10/1991 | Bormann et al. . |
| 5,206,248 | 4/1993 | Smith ................................ 514/289 |
| 5,262,162 | 11/1993 | Bormann et al. . |
| 5,382,601 | 1/1995 | Nürnberg et al. . |
| 5,455,279 | 10/1995 | Lipton ................................ 514/742 |
| 5,602,150 | 2/1997 | Lidsky . |
| 5,604,198 | 2/1997 | Poduslo et al. ...................... 514/6 |
| 5,614,560 | 3/1997 | Lipton . |
| 5,670,477 | 9/1997 | Poduslo et al. ...................... 514/6 |
| 5,747,545 | 5/1998 | Lipton ................................ 514/742 |

OTHER PUBLICATIONS

Alexander, et al., "Serum Calcium and Magnesium in Schizophrenia: Relationship to Clinical Phenomena and Neuroleptic Treatment" Brit. F. Psychiat. 133:143–49, 1978.
Ananth, et al., "Meige's Syndrome Associated with Neuroleptic Treatment", Am J Psychiatry 145:513–515, Apr., 1988.
Andreassen, et al., "Tardive Dyskinesia: Behavioral Effects of Repeated Intracerebroventricular Haloperidol Injections in Rats Do Not Confirm the Kindling Hypothesis", Pharmacology Biochemistry and Behavior, 49:309–312, 1994.
Andrew, "Clinical Relationship of Extrapyramidal Symptoms and Tardive Dyskinesia", Can, J. Psych., 39:576–580, 1994.
Arthurs, et al., "Treatment of Blepharospasm with Medication, Surgery and Type A Botulinum Toxin" Can J Ophthalmol , 22:24–28, 1987.
Athanassenas, et al., "Serum Calcium and Magnesium Levels in Chronic Schizophrenics", Journal of Clinical Psychopharmacology, 3:212–216, Aug., 1983.
Bezchilbynk–Butler et al., "Antiparkinsonian Drugs in the Treatment of Neurolepti–Induced Extrapyramidal Symptoms", Can. J. Psych.,m 39:74–84, 1994.

Boumans et al., "Is the Social Acceptability of Psychiatric Patients Decreased by Orofacial Dyskinesia?", Schizo Bull, 20:339–344, 1994.
Britton, et al., "Dextromethorphan Protects Against Cerebral Injury Following Transient, But Not Permanent, Focal Ischemia in Rats", Life Sciences, 60:1729–1740, 1997.
Buchel et al., "Oral Tardive Dyskinesia: Validation of a Measuring Device Using Digital Image Processing", Psychopharmacology–Berl, 117:162:165, 1995.
Casey, et al., "Pharmacology of Blepharospasm–Oromandibular Dystonia Syndrome", Neurology 30:690–695, Jul., 1980.
Chakos et al., "Incidence and Correlates of Tardive Dyskinesia in First Episide of Schizophrenia", Arch Gen Psychiatry, 53:313–319, 1996.
Chappell, et al., "Future Therapies of Tourette Syndrome", Neurologic Clinics of North America, 15:429–450, May, 1997.
Chen, et al., "Focal Dystonia and Repetitive Motion Disorders", Clinical Orthopaedics and Related Research, 351:102–106, Jun., 1998.
Dabiri, et al., "Effectiveness of Vitamin E for Treatment of Long–Term Tardive Dyskinesia", Am J Psychiatry 151:925–926, Jun., 1994.
De Leeuw, et al., Effect of Intensive IV + Oral Magnesium Supplementation on Circulating Ion Levels, Lipid Parameters and Metabolic Control in Mg–Depleted Insulin–Dependent Diabetic Patients (IDDM).
De Mattos, et al., "Aspectos Clínicos E Terapêuticos Em 64 Pacientes", Arq Neuropsiquiatr 54(1) 30–36, 1996.
Decker et al., "Amantadine Hydrochloride Treatment of Tardive Dyskinesia", Oct. 7, New England J. Med, 285:860, 1971.
Delfs et al., "Expression of Glutamic Acid Decarboxylase mRNA in Striatum and Pallidum in an Animal Model of Tardive Dyskinesia", Exp. Neurol. 133:175–188, 1995.
Dimpfel, "Effects of Memantine on Synaptic Transmission in the Hippocampus in Vitro", Arzneimittelforschung, 45:1–5, 1995.
Durlach, et al., "Magnesium Status and Ageing: An Update", Magnesium Research 11:25–42, 1997.
Egan, et al., "Treatment of Tardive Dyskinesia", Schizophrenia Bulletin, 23:583–609, 1997.

(List continued on next page.)

Primary Examiner—Keith D. MacMillan
Assistant Examiner—Vickie Y. Kim
Attorney, Agent, or Firm—Choate, Hall & Stewart; Sam Pasternack

[57] ABSTRACT

The present invention describes a novel treatment for movement disorders, including tardive dyskinesia and tardive dystonia, and focal dystonias not due to neuroleptics, including blepharospasm, Meige syndrome, and occupational dystonias. The treatment of the present invention utilizes agents that act as NMDA-type glutamate receptor antagonists The invention also involves the use of an ion channel blocking agent to augment the therapeutic action of the drug treatments described. A particularly preferred ion channel blocking agent is magnesium.

52 Claims, No Drawings

OTHER PUBLICATIONS

Ema, et al., "Alcohol–Induced Vascular Damage of Brain Is Ameliorated by Administration of Magnesium" Alcohol, 15:95–103, 1998.

Erdo et al., "Memantine is Highly Potent in Protecting Cortical Cultures against Excitotoxoic Cell Death Evoked by Glutamate and N–Methyl–D–Aspartate", Eur. J. Pharmacol, 198:215–217, 1991.

Esper, et al., "Adult–Onset Focal Dystonias: Presentation and Treatment Options" Tennessee Medicine, 18–20, Jan., 1997.

Fariello, et al., "Homotaurine (3 Aminopropanesulfonic Acid; 3APS) Protects From the Convulsant and Cytotoxic Effect of Systemically Administered Kainic Acid" Neurology 32:241–245, 1982.

Galardi, et al., "Basal Ganglia and Thalamo–Cortical Hypermetabolism in Patients with Spasmodic Torticollis", Acta Neurol Scand 94:172–176, 1996.

Gámez, et al., Serum Concentration and Dietary Intake of Mg and Ca in Institutionalized Elderly People.

Gao et al., "Tiagabine Inhibits Haloperidol–Induced Oral Dyskinesias in Rats", J. Neural Transmission, 95:63–69, 1994.

Gardos, et al., "The Treatment of Tardive Dyskinesias", Psychopharmacology, 1503–1511, 1995.

Greensmith, et al., "Magnesium Ions Reduce Motoneuron Death Following Nerve Injury or Exposure to N–Methyl–D–Aspartate In The Developing Rat", Neuroscience 68:807–812, 1995.

Gullestad, et al., "Magnesium Status in Health Free–Living Elderly Norwegians", Journal of the American College of Nutrition, 13:45–50, 1994.

Hallett, et al., "The Neurophysiology of Dystonia", Arch Neurol, 55:601–603, May, 1998.

Hayashi et al., "Prevalence of and Risk Factors for Respiratory Dyskinesia", Clin. Neuropharmacol, 19:390–398, 1996.

Heath, et al., "Neuroprotective Effects of $MgSO_4$ and $MgCl_2$ in Closed Head Injury: A Comparative Phosphorus NMR Study", Journal of Neurotrauma, 15:183–189, 1998.

Hoane, et al., "Preoperative Regimens of Magnesium Facilitate Recovery of Function and Prevent Subcortical Atrophy Following Lesions of the Rat Sensorimotor Cortex", Brain Research Bulletin, 45:45–51, 1998.

Holds, et al., "Facial Dystonia, Essential Blepharospasm and Hemifacial Spasm", AFP, 43(6): 2113–2120, Jun., 1991.

Imamura et al., "Improved Preservation with Amantadine", Abstract, No–To–Shinkei, 46:556–562, 1994.

Jacoby, et al., "Diltiazem Reduces the Contractility of Extraocular Muscles in Vitro and In Vivo", Investigative Ophthalmology & Visual Science, 31:569–576, Mar. 1990.

Jankovic, J. "Treatment of Hyperkinetic Movement Disorders with Tetrabenazine A Double–Blind Crossover Study", Ann Neurol 11:41–47, 1982.

Jankovic, J. "Blepharospasm and Orofacial–Cervical Dystonia: Clinical and Pharmacological Findings in 100 Patients", Ann Neurol 13:402–411, 1983.

Jankovic, J. "Botulinum Toxin in the Treatment of Dystonic Tics", Movement Disorders, 9:347–349, 1994.

Jeste et al., "Risk of Tardive Dyskinesia in Older Patients. A Prospective Longitudinal Study of 266 Outpatients", Arch Gen Psychiatry, 52:756–765, 1995.

Keilhoff et al., "Memantine Prevents Quinolinic Acid–Induced Hippocampal Damage", Eur. J. Pharmacol, 219:451–454, 1992.

Kirov, et al., "Plasma Magnesium Levels in a Population of Psychiatric Patients: Correlations with Symptoms", Neuropsychobiology 30:73–78, 1994.

Kornhuber et al., "New Therapeutic Possibilities with Low–Affinity NMDA Receptor Antagonists", Abstract, Nervenarzt, 67:77–82, 1996.

Krieglstein, et al., "Apparent Independent Action of Nimodipine and Glutamate Antagonists to Protect Cultured Neurons Against Glutamate–Induced Damage", Neuropharmacology, 35, 1737–1742, 1996.

Kurata, et al., "Meige's Syndrome During Long–Term Neuroleptic Treatment", Jpn J. Psychiatr Neurol 43:627–631, 1989.

Kurlan, R. "Treatment of Tics", Neurologic Clinics of North, May, 1997.

Lam et al., Vitamin E in the Treatment of Tardive Dyskinesia: A Replication Study, J. Nerv. Ment Dism, 182:113–114, 1994.

Latimer, "Tardive Dyskinesia: A Review", Abstract, Can J. Psych, 40:S49–54, 1995.

Lichter, et al., "Predictors of Clonidine Response in Tourette Syndrome: Implications and Inferences", Journal of Child Neurology 11:93–97, Mar., 1996.

Lipski, et al., "A Study of Nutritional Deficits of Long–Stay Geriatric Patients", Age and Ageing 22:244–255, 1993.

Lohr et al., "A Double–Blind Placebo–Controlled Study of Vitamin E Treatment of Tardive Dyskinesia", J. Clin. Psychiatry, 57:167–173, 1996.

Lombardi, J. "Opposite Effects of 2–Aminoethanesulfonic Acid (Taurine) and Aminomethanesulfonic Acid on Calcium Ion Uptake in Rat Retinal Preparations," European Journal of Pharmacology, 110(1985) 385–387.

Martin, et al., "Comparison of Inorganic Elements from Autopsy Tissue of Young and Elderly Subjects" J. Trace Elem. Elecrolytes Health Dis. vol. 5, 1991, pp. 203–211.

Mauriello, et a.., "Treatment Selections of 239 Patients with Blepharospasm and Meige Syndrome over 11 Years", Br. J. Ophthamaol, 80(12):1073–1076, Dec., 1996.

Mauriello, et al., "Treatment Choices of 119 Patients with Hemifacial Spasm over 11 Years", Clinical Neurology and Neurosurgery, 98: 213–216, Aug. 1996.

Meshul, et al., "Correlation of Vacuous Chewing Movements with Morphological Changes in Rats Following 1–Year Treatment with Haloperidol", Psychopharmacology 125:238–247, 1996.

Micheli, et al., "Continuous Dopaminergic Stimulation in Cranial Dystonia" Clinical Neuropharmacology, 11: 241–249, 1988.

Muir, K. "New Experimental and Clinical Data on the Efficacy of Pharmacological Magnesium Infusions and Cerebral Infarcts", Magnesium Research, 11:43–56, 1998.

Muller et al., "Noncompetitive NMDA Receptor Antagonists with Fast Open–Channel Blocking Kinetics and Strong Voltage–Dependency as Potential Therapeutic Agents for Alzheimer's Dementia", Pharmacopsychiatry,m 28:113–124, 1995.

Pahl et al., "Positron–Emission Tomography in Tardive Dyskinesia", J. Neuropsych Clin. Neurosci, 7:457–465, 1995.

Panula–Lehto, et al., "Effects of Taurine, Homotaurine and GABA on Hypothalamic and Striatal Dopamine Metabolism" Naunyn–Schmiedeberg's Arch Pharmacol 346:57–62, 1992.

Perlmutter, et al., "Decreased [$^{18}$F] Spiperone Binding in Putamen in Idiopathic Focal Dystonia", The Journal of Neuroscience, 17:843–850, Jan., 1997.

Raja, "The Treatment of Tardive Dyskinesia", Abstract, Schweiz Arch Neurol Psychiatr, 47:13–18, 1996.

Ransmayr, et al., "Pharmacological Study in Meige's Syndrome with Predominant Blepharospasm", Clinical Neuropharmacology, 11:68–76, 1988.

Rouhani, et al., "Effects of Muscimol or Homotaurine on Sleep–Wake States in Alcohol–Dependent Rats During Withdrawal", Pharmacology Biochemistry and Behavior, 59: 955–960, 1998.

Rotrosen, et al., "Antioxidant Treatment of Tardive Dyskinesia", Prostaglandins, Leukotrienes and Essential Fatty Acids 55: 77–81, 1996.

Sachdev, P. "Blinking–Blepharospasm After Long–Term Neuroleptic Treatment", The Medical Journal of Australia, 150:341–343, Mar. 20, 1989.

Sachdev et al., "Negative Symptoms, Cognitive Dysfunction, Tardive Akathisia and Tardive Dyskinesia", Acta Psychiatr Scand, 93:451–459, 1996.

Sanberg, et al., "Nicotine for the Treatment of Tourette's Syndrome" Pharmacol, Ther. 74:21–25, 1997.

SandyK, R. "Blepharospasm—Successful Treatment with Baclofen and Sodium Valproate", SA Medical Journal 64:955–956, 1983.

Sano et al., "A Controlled Trial of Selegiline, Alpha–Tocopherol, or Both as Treatment for Alzheimer's Disease", The New England Journal of Medicine, vol. 336, No. 17, pp. 1216–1247, Apr. 24, 1997.

Scahill, et al., "Fluoxetine Has No Marked Effect on Tic Symptoms in Patients with Tourette's Syndrome: A Double–Blind Placebo–Controlled Study", Journal of Child and Adolescent Psychopharmacology, 7:75–85, 1997.

Schulz et al., "Neuroprotective Strategies for Treatment of Lesions Produced by Mitochondrial Toxins: Implications for Neurodegenerative Diseases", Neuroscience, 71:1043–1048, 1996.

Shane, et al., "Magnesium Deficiency in Alcohol Addiction and Withdrawal", Magnes Trace Elem. 92:10, 263–268, 1991.

Silver, et al., "Case Study: Long–Term Potentiation of Neuroleptics with Transdermal Nicotine in Tourette's Syndrome", J. Am. Acad. Child Adolesc. Psychiatry, 35;1631–1636, Dec., 1996.

Steingard, et al., "Adjunctive Clonazepam Treatment of Tic Symptoms in Children with Comorbid Tic Disorders and ADHD", J. Am. Acad. Child Adolesc. Psychiatry, 33: 394–399, Mar./Apr., 1994.

Silver et al., "No Difference in the Effect of Biperiden and Amantadine on Parkinsonian and Tardive Dyskinesia–type Involuntry Movements: A Double–Blind Crossover, Placebo–Controlled Study in Medicated Chronic Schizophrenic Patients", Abstract, J. Clin. Psychiatry, 56:167–170, 1995.

Stoessl, "Effects of Ethanol in a Putative Rodent Model of Tardive Dyskinesia", Pharmacol Biochem Behav, 54:541–546, 1996.

Swartz, "Tardive Psychopathology", Neuropsychobiology, 43:115–119, 1995.

Tsai, et al., "Markers of Glutamatergic Neurotransmission and Oxidative Stress Associated with Tardive Dyskinesia", Am J Psychiatry 155:1207–1213, Sep., 1998.

Tirelli et al., "Differential Effects of Direct and Indirect Dopamine Agonists on the Induction of Gnawing in C57B1/6J Mice", J. Pharmacol Exp. Ther., 273:7–15, 1995.

Vale et al., "Amantadine for Dyskinesia Tarda", New Eng. J. Med., 284:673, 1971.

Vanický, et al., "Neurodegeneration Induced by Reversed Microdialysis of NMDA; a Quantitative Model for Excitotoxicity in Vivo", Brain Research, 789:347–350, 1998.

Van–Rekum et al., "N of 1 Study: Amantadine for the Amotivational Syndrome in a Patient with Traumatic Brain Injury", Brain Inj. 9:49–53, 1995.

Waddington et al., "Cognitive Dysfunction in Chronic Schizophrenia Followed Prospectively Over 10 Years and Its Longitudinal Relationship to the Emergence of Tardive Dyskinesia", Psychol Med, 26:681–688, 1996.

Weller, et al., "MK–801 and Memantine Protect Cultured Neurons From Glutamate Toxicity Induced by Glutamate Carboxypeptidase–Mediated Cleavage of Methotrexate" European Journal of Pharmacology—Environmental Toxicology and Pharmacology Section, 248:303–312, 1993.

Wenk et al., "MK–801, Memantine and Amantadine show Neuroprotective Activity in the Nucleus Basalis Magnocellularis", Eur. J. Pharmacol, Eur. J. Pharmacol, 293:267–270, 1995.

Yassa, et al., "Plasma Magnesium in Chromic Schizophrenia", Int. Pharmacopsychiat. 14:57–64, 1979.

Ziemann, et al., "Decreased Motor Inhibition in Tourette's Disorder: Evidence From Transcranial Magnetic Stimulation", Am J Psychiatry, 154:1277–1284, 1997.

Zorbas, et al., "Daily Magnesium Supplementation of Serum and Urinary Magnesium Changes in Rats During Prolonged Restriction of Motor Activity", Biological Trace Element Research, 58:103–115, 1997.

Richter et al., Antidystonic effects of the NMDA receptor . . . , Neuroscience Letters, vol. 133(1), p. 57–60, 1991.

METHODS OF TREATING TARDIVE DYSKINESIA AND OTHER MOVEMENT DISORDERS USING NMDA RECEPTOR ANTAGONISTS

PRIORITY INFORMATION

The present application is a Continuation-in-part of application Ser. No. 08/861,801, filed May 22, 1997, now U.S. Pat. No. 5,868,580 the entire contents of which are incorporated herein by reference.

BACKGROUND OF THE INVENTION

This invention concerns the treatment of two major types of movement disorders 1) tardive dyskinesia (TD), tardive dystonia and related movement disorders, induced by exposure to neuroleptic (antipsychotic) drugs; 2) focal dystonias not related to medications, including blepharospasm, Meige syndrome, torticollis, spasmodic dysphonia, and writer's cramp; and 3) tics, including multiple tics and Gilles de la Tourette syndrome (TS).

Movement disorders affect a significant portion of the population, causing disability as well as distress. Tardive dyskinesia (TD) is a chronic disorder of the nervous system, characterized by involuntary, irregular rhythmic movements of the mouth, tongue, and facial muscles. The upper extremities also can be involved. These movements may be accompanied, to a variable extent, by other involuntary movements and movement disorders. These include rocking, writhing, or twisting movements of the trunk (tardive dystonia), forcible eye closure (tardive blepharospasm), an irresistible impulse to move continually (tardive akathisia), jerking movements of the neck (tardive spasmodic torticollis), and disrupted respiratory movements (respiratory dyskinesia). The vast majority of TD cases are caused by the prolonged use of antipsychotic drugs (neuroleptics). A relatively small number are caused by the use of other medications, such as metoclopramide, that, like neuroleptics, block dopamine receptors. TD often manifests or worsens in severity after neuroleptic drug therapy is discontinued. Resumption of neuroleptic therapy will temporarily suppress the involuntary movements, but may aggravate them in the long run.

TD is also associated with a variable degree of cognitive impairment. Cognitive dysfunction associated with TD may involve attention, concentration, memory, or executive functions such as judgment or abstract reasoning. (see, e.g., Sachdev et al., *Acta Psychiatr Scand* 93:451, 1996; Waddington & Youssef, *Psychol. Med.* 26:681, 1996; Swartz, *Neuropsychobiology* 32:115, 1995). The cognitive impairment associated with TD usually is seen as a marker of underlying differences in brain function that predispose the patient to TD. However, it may also be due to the TD itself, and may be either irreversible, or partially reversible if the TD is successfully treated.

Tardive dyskinesia (TD) affects approximately 15–20% of patients treated with neuroleptic drugs (Khot et al., *Neuroleptics and Classic Tardive Dyskinesia*, in Lang A E, Weiner W J (eds.): *Drug Induced Movement Disorders*, Futura Publishing Co., 1992, p. 121–166). Neuroleptics are used to treat several common psychiatric disorders, including schizophrenia and related psychoses (estimated prevalence 1%), mood disorders with psychotic features (estimated minimum prevalence 0.5%), and Alzheimer's disease with psychosis or agitation (estimated minimum prevalence at 0.5%. Assuming that half of those in need of neuroleptic treatment receive it, it follows that TD affects hundreds of thousands of people in the United States alone. The cumulative incidence of TD is substantially higher in women, in older people, and in those being treated with neuroleptics for conditions other than schizophrenia, such as bipolar disorder (manic-depressive illness) (see, e.g., Hayashi et al., *Clin. Neuropharmacol*, 19:390, 1996; Jeste et al., *Arch. Gen. Psychiatry*, 52:756, 1995). Unlike the acute motor side effects of neuroleptic drugs, TD does not respond in general to antiparkinson drugs (Decker et al., *New Eng. J. Med.*, Oct. 7, p. 861, 1971).

The focal dystonias are a group of movement disorders involving the intermittent sustained contraction specific muscle groups, resulting in recurrent abnormal posturing of some part of the body. The most common is spasmodic torticollis, which involves twisting of the neck. Other examples are blepharospasm, which involves involuntary eye closure or excessively forceful blinking, and writer's cramp, which involves contraction of the muscles of the hand. Another less common focal dystonias involve the laryngeal muscles (spasmodic dysphonia). Other relatively rare dystonias involve muscle groups specific to a particular occupation, such as playing the violin. The prevalence of focal dystonias in one US county was estimated as 287 per million (Monroe County Study); this suggests that at least 70,000 people are affected in the US alone. Blepharospasm alone affects more than 25,000 people (Source: US FDA Web Site; page on Orphan Drug Act).

Tics are estimated to affect 1% to 13% of boys and 1% to 11% of girls, the male-female ratio being less than 2 to 1. Approximately 5% of children between the ages of 7 and 11 years are affected with tic behavior (Leckman et al., *Neuropsychiatry of the Bas. Gang*, December, 20(4): 839–861, 1997). The estimated prevalence of multiple tics with vocalization, i.e. Tourette's syndrome, varies among different reports, ranging from 5 per 10,000 to 5 per 1,000. Tourette's syndrome is 3–4 times more common in boys than girls and 10 times more common in children and adolescents than in adults (Leckman et al., supra; Esper et al, *Tenn. Med., January*, 90:18–20, 1997).

A tic is an abrupt repetitive movement, gesture, or utterance that often mimics a normal type of behavior. Motor tics include movements such as eye blinking, head jerks or shoulder shrugs, but can vary to more complex purposive appearing behaviors such as facial expressions of emotion or meaningful gestures of the arms and head. In extreme cases, the movement can be obscene (copropraxia) or self injurious. Phonic or vocal tics range from throat clearing sounds to complex vocalizations and speech, sometimes with coprolalia (obscene speech) (Leckman et al., supra). Tics are irregular in time, though consistent regarding the muscle groups involved. Characteristically, they can be suppressed for a short time by voluntary effort.

Gilles de la Tourette syndrome (TS) is the most severe tic disorder. Patients with TS have multiple tics, including at least one vocal (phonic) tic. TS becomes apparent in early childhood with the presentation of simple motor tics, for example, eye blinking or head jerks. Initially, tics may come and go, but in time tics become persistent and severe and begin to have adverse effects on the child and the child's family. Phonic tics present, on average, 1 to 2 years after the onset of motor tics. By the age of 10, most children have developed an awareness of the premonitory urges that frequently precede a tic. Such premonitions may enable the individual to voluntary suppress the tic, yet premonition unfortunately adds to the discomfort associated with having the disorder. By late adolescence/early adulthood tic disorders can improve significantly in certain individuals.

However, adults who continue to suffer from tics often have particularly severe and debilitating symptoms. (Leckman et al., supra).

The pathophysiology of movement disorders, specifically TD, TD has not been established definitively. It is well known that blockade of dopamine receptors will lead to an increased number of dopamine receptors, and therefore to an increased sensitivity to dopamine of striatal neurons. (see e.g., Andrews, *Can J Psych* 39:576, 1994; Casey, in *Psychopharmacology: The Fourth Generation of Progress*, Raven Press, 1995). The first major hypothesis about the pathophysiology of TD was that TD was the result of this hypersensitivity of striatal neurons to dopamine. In support of the "dopamine supersensitivity" hypothesis, it is noted that dopamine agonists can aggravate the disorder (Bezchibnyk-Butler & Remington, *Can J. Psych,*. 39:74, 1994). However, the dopamine supersensitivity hypothesis is not compatible with the observation that TD and Parkinsonism (a dopamine deficiency state) often exist together in the same patient.

Other studies have suggested that irreversible cases of TD may be related to excitotoxic damage to the basal ganglia (Andreassen & Jorgensen, *Pharmacol. Biochem. Behav.*, 49(2):309–312, 1994; Tsai et al.,: *Am J Psych*, September 155:9, 1207–13, 1998). An acquired deficiency of the inhibitory neurotransmitter GABA has also been implicated in the development of TD.

A widely-studied animal mode of TD, that of vacuous chewing movements (VCM) in rats, has also yielded evidence for a glutamate-based excitotoxic mechanism in the development of the disorder (Meshul et al; *Psychopharmacology* (Berl), 125:238–47, 1996 June; Andreassen et al; *Br J Pharmacol*, 199:751–7, 1996 October) When administered to rats with VCM, ethanol acutely decreases the animal's orofacial movements. This effect is prevented if the rats are pre-treated with a benzodiazepine inverse agonist, suggesting that it is mediated by stimulation of GABA-A receptors by ethanol (Stoessl, *Pharmacol. Biochem. Behav.* July, 54:541–6, 1996 July) Stoessl suggests that "GABAergic stimulation" deserves further investigation in the treatment of TD. He does not, however, advance the idea of treating TD with NMDA antagonists, nor suggest using memantine as a treatment for TD.

The physical manifestations of TD can resemble movement disorders associated with degenerative diseases such as Huntington's disease and Parkinson's disease. Patients with TD can show chorea (quick, irregular movements of the extremities) indistinguishable from that seen in cases of Huntington's disease. Neck, trunk and limb movements of TD can be indistinguishable from those of the peak-dose dyskinesia associated with prolonged treatment of Parkinsons disease with levodopa. The physical manifestations of tardive dystonia are nearly identical to the manifestations of the idiopathic dystonias, i.e., those not related to exposure to dopamine antagonists. (See the further discussion below.)

It is evident that similar mechanisms may be involved in the pathophysiology of tardive movement disorders and idiopathic focal dystonias. Positron emission tomography has shown that one specific dystonia, torticollis, is associated with neuronal hypermetabolism in the basal at ganglia. It has been hypothesized that hyperactivity of a motor control loop involving the cerebral cortex, basal ganglia, and thalamus is responsible for the abnormal postures and movements (i.e. movements into and out of abnormal postures) characteristic of dystonia (Galardi et al., *Acta. Neurol Scand*, September, 94:172–6, 1996). Other studies have shown abnormal dopaminergic transmission or receptor function in patients with dystonia (see, e.g. Perlmutter et al., *J Neurosci*, Jan. 15, 17:843–50, 1997). Of note, both too much or too little dopamine may be associated with dystonia, since patients with Parkinson's disease and dystonia can have the problem both at peak and trough levels of levodopa (Hallett, *Arch. Neurol*. May, 55:601–3, 1998). Although memantine has dopamine agonist activity, memantine has not been suggested as a treatment for focal dystonias.

The pathophysiology of tic disorders like, that of TD, has not yet been established difinitively, although several plausible hypotheses have been set forth. The pathophysiology of tic disorder resembles the mechanism that may be involved in the pathophysiology of tic disorders and focal dystonias. Excessive activity of a cortical-striatal-pallidal-thalamic-cortical sensorimotor loop has been implicated in the lack of motor impulse control associated with tic disorders (Zambian et al., *Am. J. Psychiatry*, Vol 154, September, 1997; Leckman et al., supra). This hyperactivity may reflect excessive dopaminergic activity in the striatum, or a relative deficiency of inhibitory transmission. While dysfunction of the basal ganglia or their connections is likely to be present, the basal ganglia, thalamus, and motor cortex are anatomically normal in most cases.

Treatment of TD

Recent research suggests that Vitamin E can reduce symptoms of TD modestly (Lohr & Caliguiri, *J Clin Psychiatry* 57; 167, 1996; Dabiri et al. *Am. J. Psychiatry*, June, 151(6):925–926, 1994). GABA agonists such as baclofen and various benzodiazepines have also been the subject of some positive reports and are widely used in practice to ameliorate the symptoms of TD, probably because their low toxicity justifies their use despite their limited efficacy. (Gardos & Cole, *Psychopharmacology: The Fourth Generation of Progress*, eds. Bloom and Kupfer, pp. 1503–1510, 1995). The latter review cited reports of variable benefits associated with other agents including propranolol, clonidine, cholinergic agonists, buspirone and calcium-channel antagonists. However, none of these has become a generally accepted treatment for either the movement or cognitive disorders associated with TD. (The author has had some success in treating TD with nimodipine, a calcium-channel antagonist with particularly good penetration of the CNS.)

In U.S. Pat. No. 5,602,150, by Lidsky et al., it was proposed that the emergence of TD in patients receiving neuroleptics might be prevented by simultaneously administering taurine or taurine derivatives. Lidsky based his invention on the theory that TD is due to excitotoxic damage, and that taurine and taurine derivatives would protect patients against this damage. The recommendation of taurine is based on studies in a single animal model. The experiments reported do not deal with any therapeutic effects of taurine on established movements, either in the presence of continued neuroleptic administration or otherwise. Neither the patent nor the experiments cited in it predict or imply that taurine or derivatives will be beneficial for established movement disorders. Moreover, the mechanism proposed by Lidsky et al., (supra) is based on long-term neuroprotection. He neither infers, asserts, suggests nor suggests that taurine or taurine derivatives might have any immediate, short-term effect on movement disorders.

Memantine is a drug approved in Europe for treatment of Parkinson's disease. Memantine, a congener of amantadine, is a N-methyl-D-aspartate type glutamate receptor blocker ("NMDA receptor antagonist" or "NMDA receptor blocker") as well as a dopamine agonist. Although memantine has been reported to alleviate some of the dyskinetic movements that can be seen in treated Parkinson's disease, there are no reports of its use in humans to treat tardive dyskinesia, and at least one widely-reputed expert in the field of TD expressed surprise that any anti-Parkinson's drug would be an effective agent against TD (Dilip Jeste, M. D., personal communication, 1997).

In U.S. Pat. No. 4,122,193, it is reported that 1,3,5-trisubstituted adamantane, including 1-amino-3,5-dimethyl-adamantane is useful in the treatment of hyperkinesis in rats. The agent is also recommended as a treatment generally for hyperkinesis, in the context of Parkinson's disease, head tremors, thalamic tension conditions, and spastic conditions, and for "the activation of patients with akinetic cerebroorganic conditions". It is notable that, unlike TD, none of the underlying conditions described in that patent as the context of the hyperkinesis to be treated, is thought to be aggravated by dopamine agonists. Moreover, there is no recognition in the reference that 1-amino-3,5-dimethyl-adamantane acts as a NMDA-receptor blocker. Instead, the disclosure indicates that 1,3,5-trisubstituted adamantane compounds influence catecholamine metabolism, for instance by freeing dopamine or stimulating the receptors. This latter aspect suggests that the authors did not recognize that memantine could be an effective treatment of TD, for which administration of dopamine agonists in general goes against expert opinion.

In co-pending, commonly-owned applications Ser. Nos., 08/861,801 and 09/006,641, incorporated herein by reference, treatments with memantine (a congener of amantadine and a N-methyl-D-aspartate type (NMDA) receptor blocker as well as a dopamine agonist), and acamprosate (a calcium salt of a derivative of the amino acid taurine and an indirect NMDA antagonist and GABA-A agonist), were advanced as effective treatments for both the movement and the cognitive disorders associated with TD, and were reported to be dramatically effective in several severely affected individuals. The cases described in those patent applications contain the first reports of the use of memantine for the treatment of TD.

Treatment of Focal Dystonia

As noted above, a focal dystonia is a movement disorder involving recurrent abnormal posturing of some part of the body. The spasms of focal dystonia can last many seconds at a time, causing major disruption of the function of the affected area. No systemic drug therapy is generally effective, but some drugs give partial relief to some patients. Those most often prescribed are anticholinergics, baclofen, benzodiazepines, and dopamine agonists and antagonists. The most consistently effective treatment is the injection of botulinum toxin into affected muscles.

The various focal dystonias tend to respond to the same drugs (i.e., treatments that are helpful for one focal dystonia generally have been helpful for others.) (Chen, *Clin. Orthop*, June, 102–6, 1998; Esper et al; *Tenn. Med*, January, 90:18–20, 1997; De Mattos et al., *Arq. Neuropsychiatry*, March 54:30–6, 1996). Published clinical experience to date suggests that a new treatment that reduced the involuntary movements of one focal dystonia would be likely to do the same for the involuntary movements of another. Furthermore, the common symptoms, signs, and responses to medication of spontaneous (idiopathic) dystonia and neuroleptic-induced dystonia suggest that an effective treatment for a drug-induced focal dystonia will be effective for the same dystonia occurring spontaneously.

Blepharospasm, one of the focal dystonias, is a condition that involves continually recurring involuntary eye closure or excessive forceful blinking. Blepharospasm is one of the most common disorders of oculomotor function. It is variably regarded as a facial dyskinesia or a facial dystonia. When it occurs together with dystonia of the oral and mandibular regions, with or without involvement of the neck, it is referred to as Meige syndrome. Blepharospasm can significantly impair visual function. Patients can become unable to read, to drive an automobile, or to do any skilled work requiring visual control. Blepharospasm can occur spontaneously (idiopathic blepharospasm) and with a prevalence that increases with increasing age; most cases arise in the fifth and sixth decades of life (Holds et al., *Am. Fam. Physician*, June, 43:2113–20, 1991). It also can occur as a sequel to neuroleptic drug treatment (Ananth et al., *Am. J. Psychiatry*, April, 145:513–5, 1988; Kurata et al., *Jpn. J. Psychiatry. Neurol.*, December, 43:627–31, 1989; Sachdev et al., *Med. J. Aust.*, Mar. 20, 150:341–3, 1989) and perhaps treatment with other classes of psychotropic drugs (Mauriello et al., *J Neuropathol*, June, 18:153–7, 1998), either alone or in conjunction with tardive dyskinesia or other forms of tardive dystonia. Another report of 19 patients with severe tardive dyskinesia, stated that frequent eye blinking was the most frequent prodromal sign of the disorder (Gardos et al., supra, 1988). The oculomotor phenomena of idiopathic blepharospasm and Meige syndrome are identical with those seen in cases induced by neuroleptic treatment. Differences between idiopathic blepharospasm and tardive blepharospasm do not involve the ocular movements themselves. (Observed differences have involved family history and the likelihood that other non-ocular involuntary movements will be present.)

Though many substances have been tested for their ability to relieve blepharospasm, injection of botulinum toxin into orbicularis oculi muscles is the mainstay of treatment (Mauriello et al., Br. J. Ophthalmol, December, 80:1073–6, 1996). These injections weaken the muscles responsible for eye closure, thereby mitigating the involuntary movements of those muscles. They may also indirectly influence oculomotor control by the central nervous system, by altering the input from motor nerve afferents. Botulinum toxin injections have become treatment of choice because they ameliorate symptoms in approximately 80% of patients—a much greater proportion than benefit from the numerous systemic drug treatments tried to date.

Movements associated with blepharospasm do not respond well to the systemic drug treatments employed to date. In one large case series, only 22% of blepharospasm patients treated with systemic medications got marked and persistent relief (Jankovic et al., *Mov. Disord.*, May, 9:347–349,1983). In another report, of the 13 patients with blepharospasm who did not do well with botulinum toxin injections, only 2 showed any improvement when given systemic drug therapy (Mauriello et al., *Clin. Neurol. Neurosurg.*, August, 98:213–6, 1996)). Even botulinum toxin injections are not always efficacious. Surgery is sometimes recommended for patients who do not get relief from botulinum toxin injections (Elston et al., *J. Neurol*, January, 239:5–8, 1992).

Of the numerous systemic treatments tried for the treatment of blepharospasm, (see, for example, Arthurs et al., *Can. J. Ophthalmol*; February, 22:24–8, 1987; Casey et al., *Neurology*, July, 30:690–5, 1980; Jacoby et al., *Invest. Ophthalmol. Vis. Sci.*, March, 31:569–76, 1990; Michaeli et al., *Clin. Neuropharmacol.*, June, 11:241–9, 1988; Ransmayr et al., *Clin. Neuropharmacol.*, February, 11:68–76, 1988) clonazepam, a GABA agonist, was the only drug consistently found useful (Jankovic et al., *Ann. Neurol.*, April, 13:402–11, 1983). A combination of two GABA agonist agents, valproate and baclofen, was efficacious in a single case (Sandyk, et al., *S Afr Med J*, December, 64:955–6, 1983). Tetrabenazine, a dopamine depleting agent, alleviated involuntary movements in 4 of 6 patients with Meige syndrome, but the patients had many undesirable side effects including drowsiness, drooling and Parkinsonism (Jankovic, et al., *Ann Neurol*, January, 11:41–7, 1982). Because of such unpleasant side effects, tetrabenazine has not become a widely-used treatment for blepharospasm, tics or even tardive dyskinesia, despite the absence of other generally effective treatments for these conditions. Neuroleptics sometimes relieve symptoms of blepharospasm, but they do so less well than tetrabenazine, and patients treated with them run the risk of developing TD or other tardive movement disorders. In sum, though drugs that reduce dopaminergic transmission have been employed with some benefit in the treatment of idiopathic blepharospasm, neither type of medication has proved to be a generally satisfactory treatment.

Treatment of Tics and Tourette's Syndrome

Patients with moderate to severe motor and vocal tics are likely to require drug therapy. Many classes of neurological and psychiatric medications have been tried, but only neuroleptics, alpha-2 adrenergic agonists, and clonazepam have attained the status of standard treatments. (For recent reviews see Chappell et al., *Neur. Clin. of North Am.*, 15(2), May 1997; Kurlan, *Neurol. Clin.*, May, 15:403–409, 1997; Lichter et al., *J. Child Neur.*, 11(2), March, 1996; Leckman et al., supra; Esper et al, *Tenn. Med.*, January, 90:18–20, 1997; Scahill et al., *J. Child Adolesc Phychopharcmacol*, 7(2), 1997; incorporated herein by reference). Unfortunately, all three of the commonly-used treatment for TS have significant drawbacks.

The most common therapies used for the treatment of tic disorders are the neuroleptics (i.e. dopamine antagonist antipsychotic drugs). Within this category, haloperidol and pimozide are most often used in the United States. Neuroleptic treatment usually will suppress the involuntary movements of tic disorders, with up to 85% of patients experiencing relief—Esper et al., supra). The side effects of neuroleptic drugs include sedation, depression, parkinsonism, cognitive impairment, and tardive dyskinesia. Other tardive movement disorders can develop with prolonged use. The intolerability of side effects often leads patients to discontinue neuroleptic therapy for TS, while the risk of TD makes most physicians unwilling to use them in milder cases. Those with more severe TS must often make an unpleasant choice between distressing symptoms and distressing side effects. People with simple tics may experience emotional distress, embarrassment, impaired self-esteem, or physical injury if their tics are sufficiently violent. Yet, they usually will not be treated with neuroleptics because their side effects and long-term toxicity that are not acceptable in the treatment of relatively mild cases.

Other drug treatments for TS do not carry the risk of TD. But they are less efficacious than neuroleptics. The most common non-neuroleptic alternatives are alpha-2 adrenergic agonists such as clonidine. Unfortunately, fewer than 50% (perhaps as few as 25%) of patients treated with clonidine show clinically significant improvement of tic-related symptoms (Esper et al., supra; Chappell et al., supra). Further, many patients whose tics do respond to clonidine will have side effects that limit its use, most often hypotension or sedation.

Another non-neuroleptic treatment, clonazepam, a benzodiazepine with GABA-A and serotonergic actions, has some efficacy in the treatment of Tourette's syndrome (Steingard et al., *J. Am Acad Child Adolesc Psychiatry*, March–April, 33:394–9, 1994). Sedation and ataxia limit the dosage of clonazepam; the tolerable dose often is below that needed to suppress the patient's tics.

A new class of compounds that act as antagonists of brain serotonergic 5-HT$_2$ receptors initially showed promising results, although children and adolescents experience increase in sensitivity to side effects. (Chappell et al., supra). Additional alternatives that have received recent attention include antioxidant treatment (Rotrosen et al., *Prost. Leuk. and Ess. Fatty Acids*, 55(1 & 2), 1996), transcranial magnetic stimulation (Ziemann et al., supra), nicotine treatment (Sanberg et al., *Phamacol. Ther.*, 74(1)., 1997; Silver et al., *J. Am. Acad. Adolesc. Psychiatry*, Vol 35, December, 1996) and botulinum toxin treatment (Esper et al., supra). While each of these treatments has offered clinically significant relief to individual patients, none has replaced neuroleptics as the treatment of choice. Clearly, there is a need for additional treatments for tics and TS that do not carry the side effects and long term risks of neuroleptics.

It has been suggested, on theoretical grounds, that future therapies for Tourette's syndrome might include glutamate antagonists, although a recent article proposing their use makes no mention of any specific drugs that might fulfill this role (Chappell et al., *Neurol. Clin.* May, 15(2):429–450, 1997). 4).

Magnesium and Movement Disorders

There is considerable evidence for abnormalities of magnesium status in patients with severe mental illness (see for example, Athanassenas et al., *J. Clin. Psychopharmacol*. August, 3:212–6, 1983; Alexander et al., *Br. J. Psychiatry*, August, 133:143–9, 1978; Kirov et al., *Neuropsychobiology*, 30(2–3):73–78, 1994; Wang et al, 1997; Yassa et al., *Int. Pharmacopsychiatry*, 14(1):57–64, 1979). Alexander et al. (supra, 1978) found that those schizophrenic patients developing extrapyramidal side effects from neuroleptics had, on average, lower magnesium levels than those not having such side effects. Neuromuscular excitability and anxiety are common acute manifestations of magnesium depletion. And, there are theoretical reasons to speculate that magnesium deficiency may contribute to a wide range of neurodegenerative disorders (Durlach et al. 1997, supra). However there has been no suggestion that magnesium deficiency is a cause of tardive dyskinesia, other tardive movement disorders, blepharospasm, or other focal dystonias, or that magnesium supplementation could be used to successfully treat or prevent movement disorders, in the absence of overt magnesium deficiency manifested by tetany.

Although the present day pharmacopeia offers a variety of agents to treat the movement disorders described above, none of these agents can prevent or cure these conditions. Furthermore, the most effective systemic drug treatments often are associated with intolerable side effects. Injections of botulinum toxin can be uncomfortable, must be repeated frequently, and often lose their efficacy over time. In addition, when used to treat dystonia of an upper extremity, they may weaken muscles needed for optimal function of the hands. There remains a clear cut need for new systemic treatments for TD, other tardive movement disorders, blepharospasm, and other focal dystonias, that have greater efficacy and fewer side effects than those currently available.

SUMMARY OF THE INVENTION

The present invention provides a method for treating movement disorders including TD, other tardive movement disorders, tic disorders, blepharospasm, and other focal dystonias, in humans. In one aspect, the invention provides a method for reducing involuntary movements characteristic of patients with movement disorders by administering a pharmacological agent that decreases NMDA-type glutamate neurotransmission. In another aspect, a pharmaceutical agent is selected from the group of agents that have the ability to reduce glutamate-induced excitatory post-synaptic potentials in striatal cells. Specific instances include memantine, dextromethorphan and congeners or derivatives thereof with similar pharmacodynamic effects on NMDA-type glutamate neurotransmission, and pro-drugs that are metabolized in the liver, blood, or brain to yield active metabolites and derivatives with similar pharmacodynamic effects.

The present invention also provides a method for treating movement disorders by combining magnesium or a non-competitive NMDA receptor antagonist with memantine or another compound or mixture thereof (specifically including those enumerated in the previous paragraphs) that decreases the postsynaptic response to glutamate at NMDA-type receptors. Additionally, dextromethorphan can be combined with memantine and magnesium for the treatment of movement disorders. In preferred embodiments, magnesium is used as a non-competitive NMDA receptor antagonist. (Memantine functions as an NMDA receptor antagonist via blockade of calcium ion channels.)

The present invention demonstrates that magnesium can augment the effect of pharmacological agents used to treat movement disorders including tics and TD, and, by extension, TS and blepharospasm and other focal dystonias, whether caused by neuroleptic exposure or not. Synergistic activity is shown between magnesium and other pharmacological agents that act as NMDA receptor antagonists.

In one embodiment, any combination of agents that act as NMDA receptor antagonists, with or without magnesium, are used for treatment of movement disorders.

A pill combining an one or more agents that act as NMDA-type glutamate receptor antagonists and magnesium is proposed as a specific vehicle for the delivery of this combined therapy. In addition, other oral preparations are suggested; the mixture can be delivered in a syrup, elixir, or time release capsule. The latter is suggested as a method for prolonging the duration of action of a dose of the mixture.

DEFINITIONS

"Tardive dyskinesia": As used herein "tardive dyskinesia" is meant to include tardive dystonia and other movement disorders related to long-term neuroleptic use. The abbreviation TD may be used in place of the term "tardive dyskinesia". Also, the set of conditions comprised by TD in this application can also be referred to as "tardive dyskinesia and related tardive movement disorders".

"Blepharospasm": As used herein, "blepharospasm" includes Meige syndrome, which is a combination of blepharospasm and dystonia of the face and/or neck.

"Focal dystonia": As used herein, "focal dystonia" includes blepharospasm and Meige syndrome, spasmodic torticollis, spastic dysphonia, writer's cramp, musician's cramp and other occupational dystonias.

"Tourette's syndrome": "Tourette's syndrome" as used herein is synonymous with "Gilles de la Tourette syndromes", "Tourette syndrome", "Tourette disorder", and similar expressions. The abbreviation TS may be used in place of any of these terms.

"NMDA receptor antagonist": As used herein, "NMDA receptor antagonist" is any molecule that inhibits or diminishes the post-synaptic response of NMDA-type glutamate receptors to glutamate.

"NMDA-type glutamate neurotransmission": "NMDA-type glutamate neurotransmission" is used herein broadly, to refer to anything that would decrease NMDA-glutamate transmission, whether it acts before the synapse, at the glutamate receptor binding site, at a modulatory site such as the glycine modulatory site, within the ion channel, within the cell membrane, or inside the neuron. This also includes any substance that reduces release of glutamate at synapses with NMDA receptors, alters the binding of glutamate to NMDA receptors or alters the number or type of NMDA receptors.

"Effective": "Effective" as used herein in reference to dosage of a medication, refers to the administration of a specific amount of a pharmacologically active agent tailored to each individual patient manifesting symptoms of a particular movement disorder (e.g. TD, other tardive movement disorders, tic disorders, blepharospasm, and other focal dystonias) sufficient to cause a reduction or improvement in the patient's involuntary movements or any of the other symptoms associated with the movement disorder, with tolerable adverse effects. Symptoms of movement disorders, as referred to herein, refer not only to involuntary movements, but also to any and all impairments of physical, instrumental, social, and occupational functioning, including visual function, cognitive function, and use of the hands, that are attributable to the involuntary movements, or to the brain dysfunction that underlies them.

Experimentally, doses of memantine ranging from 10 mg to 30 mg have been shown to be effective, as have doses of dextromethorphan ranging from 30 mg four times a day to 60 mg four times a day. A person skilled in the art will recognize that the optimal dose of a pharmaceutical agent to be administered will vary from one individual to another. Dosage in individual patients should take into account the patients height, weight, rate of absorption and metabolism of the medication in question, the stage of the disorder to be treated, and what other pharmacological agents are administered concurrently.

"Movement disorder": "Movement disorder", as used herein, is used to refer to all forms of abnormal and involuntary movements. Movement disorders include, for example, tardive dyskinesia (TD), tics, Gilles de la Tourette syndrome (TS), Parkinsons disease, Huntingtons disease, and focal dystonias such as blepharospasm. Specific movement disorders that are the subject of this application include, without limitation, TD, other tardive movement disorders, blepharospasm and other focal dystonias, whether or not the latter are associated with exposure to neuroleptic drugs or other dopamine antagonists.

DETAILED DESCRIPTION OF THE INVENTION

The present invention relates to the treatment of movement disorders including, without limitation, TD, other tardive movement disorders, tics, Tourettes, blepharospasm and other focal dystonias, whether or not the latter are associated with exposure to neuroleptic drugs or other dopamine antagonists. These movement disorders likely involve some of the same physiological mechanisms and therefore will probably be responsive to the same treatments. In one aspect of the present invention, I have discovered that memantine, a drug used in the treatment of Parkinson's disease, but not contemplated for use in treatment of tardive dyskinesia, tardive dystonia, or focal dystonia whether or not related to neuroleptics or other drugs, is an effective in reducing the involuntary movements, cognitive symptoms, and functional impairment associated with tardive dyskinesia. I have also discovered that memantine is an effective treatment of tics and related tic disorders.

Several years ago, I hypothesized that TD represents a form of non-linear oscillation in neural circuits involving the basal ganglia, and that oscillation might be reduced by agents that block excitatory neurotransmission. PET scan studies have demonstrated increased metabolism in the globus pallidus and primary motor cortex in schizophrenic patients with TD, but not in those without TD (Pahl et al., *J. Neuropsych Clin Neurosci* 7:457, 1995). This suggests that TD is associated with hyperactivity in a motor control circuit, which might be part of the putative nonlinear oscillator.

As noted above, I have advanced the hypothesis that agents which act to reduce the gain in a motor control circuit through the striatum, may have a beneficial action on TD and related movement disorders including tardive movement disorders, focal dystonias, tics and Tourette's.

Without limiting the biochemical mechanism of the invention to that described here, it appears that drugs that act to reduce the gain in the hypothesized oscillator circuit would reduce the involuntary movements of tardive dyskinesia. GABA, glutamate, and dopamine are the principal neurotransmitters in the circuit. Other neurotransmitters, including norepinephrine, serotonin, acetylcholine and endogenous opiates are hypothesized to have indirect actions on the oscillator circuit. In my co-pending patent application, Ser. No. 08/861,801, the teachings of which are incorporated herein by reference, I disclosed that certain antagonists of excitatory neurotransmitters are effective in treating both the movement and cognitive disorders associated with TD, tardive dystonia, tics, and movement disorders that share a similar biochemical mechanism.

In the current invention, I disclose that memantine, an NMDA-type glutamate receptor antagonist can ameliorate TD as well as related involuntary movements and cognitive symptoms. In particular, I have demonstrated in two patients that memantine can ameliorate blepharospasm associated with a more extensive tardive movement disorder. According to the theory of the present invention, a NMDA receptor antagonist reduces the severity of the involuntary movements associated with TD. Such an NMDA-type receptor antagonist will likely alleviate focal dystonias and idiopathic focal dystonias, whether or not accompanied by other symptoms of TD, and whether or not related to exposure to neuroleptics or other dopamine receptor antagonists, based on the hypothesis that common response to several therapies implies a common physiology. For example, NMDA receptor antagonists will relieve symptoms of blepharospasm associated with TD, and by extension drug-induced blepharospasm without TD, and idiopathic blepharospasm, which are likely to share a common mechanism, in light of their response to dopamine antagonists, to GABA agonists, and to botulinum toxin injections. Dr. Gary Borodic, an expert on blepharospasm at the Harvard Medical School, states that neuroleptic-induced (tardive) blepharospasm is in general less responsive to medications than the spontaneous kind (Borodic, personal communication, 1998). If the underlying mechanisms of idiopathic and tardive blepharospasm are similar, this implies greater severity of those mechanisms in the case of tardive blepharospasm. It follows that a treatment effective for tardive blepharospasm is especially likely to be helpful for blepharospasm not associated with neuroleptic drug exposure.

Likewise, treatment with memantine will likely ameliorate symptoms associated with Meige syndrome, which is blepharospasm accompanied by dystonic movements of the neck and lower face. One of the two patients described below (Case Report 1) with TD not only had blepharospasm, but also had dystonic movements of the face and neck, permitting a diagnosis of tardive Meige syndrome. As with blepharospasm alone, Meige syndrome not associated with neuroleptics can be expected to respond at least as well to memantine as tardive Meige syndrome.

The above hypothesis regarding a motor control circuit involving glutamate (via NMDA receptors) and suggests that any drug that is an NMDA-type glutamate antagonist, with a relative lack of toxicity at effective doses, can ameliorate blepharospasm, Meige syndrome, and tardive movement disorders. Memantine is a specific example of such a drug for which I offer direct evidence of efficacy in humans (see Case Reports 1 and 2).

As noted above, GABA-A agonists alone are not particularly potent therapies of tics. Therefore, NMDA antagonism is likely a necessary part of the therapeutic effect of acamprosate. Furthermore, NMDA antagonism in itself is sufficient in treatment of tardive dyskinesia and tardive dystonia, suggesting that where tardive movement disorders are concerned, the NMDA of memantine is more important than its dopamine agonism. Evidence disclosed herein suggests that movement disorders, such as tics and Tourette's, will respond in a manner similar to tardive movement disorders to drug therapies having NMDA antagonist activity.

The hypothesis that a common response to several therapies implies common physiologic mechanism in reference to tics ant Tourette's is supported by the fact that: 1) acamproate or alleviates tardive dyskinesia, tardive dystonia and tics; and 2) memantine alleviates tardive dyskinesia and tardive dystonia; and 3) both acamprosate and memantine are NMDA-type receptor antagonist. Thus, it is logical to expect that memantine will also be helpful in the treatment of tics, including Tourette's. I disclose in the present application that memantine dramatically diminishes dyskinetic movements associated with tic disorders including both single and multiple tics. Furthermore, I propose that memantine and other agents (and congeners and derivatives thereof) with similar pharmacokinetic action, that both (i) decrease NMDA type glutamate neurotransmission, and (ii) increase dopamine receptor neurotransmission are useful in the treatment of a common and severe type of tic disorder, Tourette's syndrome, which is characterized by multiple motor and phonic tics. Case Report 5 demonstrates that a patient with a simple tic experiences a significant reduction in the frequency of the tic upon administration of memantine.

Other examples of drugs with similar effects on NMDA-type glutamate transmission include dextromethorphan, derivatives of memantine and dextromethorphan, and pro-drugs that are metabolized in the liver, blood, or brain to yield biologically active compounds with similar pharmacodynamic properties. Dextromethorphan, like memantine and amantadine, is a NMDA receptor antagonist. In one preferred embodiment of the present invention, dextromethorphan (and congeners and derivatives thereof), are administered to patients for treatment of movement disorders. There have been no reports of the use of dextromethorphan in the treatment of tardive dyskinesia, dystonia or other movement disorders.

A preferred embodiment of the present invention provides derivatives of memantine and dextromethorphan at effective doses to a patient for treatment of movement disorders.

Additionally, particularly preferred forms of memantine and dextromethorphan would be derivatives with longer durations of action, e.g. obtained through longer elimination half-lives. Such derivatives of memantine or dextromethorphan would be clinically superior to memantine or dextromethorphan, because they could be taken once daily, rather than two to four times per day, as is necessary when memantine or dextromethorphan are used. An additional approach to lengthening the duration of action of memantine, dextromethorphan or related medications is to deliver them in a time-release capsule.

In other preferred embodiments, these derivatives are used to treat dyskinesia and dystonia disorders associated with prolonged exposure to neuroleptic medications. Additionally, compositions described in the present application can be used to treat tardive dyskinesia in patients who continue to be treated with neuroleptics for persistent or chronic mental disorders, for example bipolar disorder or schizophrenia. More particularly, the present invention provides treatments that reduce the severity and duration of various related movement disorders. Another preferred embodiment of the present invention provides a treatment for focal dystonias. One example of a focal dystonia, blepharospasm, is a target for treatment in the present invention.

The present invention demonstrates relief of blepharospasm associated with tardive dyskinesia by treatment with memantine, suggesting that this and related compounds and derivatives with similar action on NMDA-type glutamate will benefit people with idiopathic blepharospasm and all other focal dystonias, whether spontaneous or induced by exposure to neuroleptic medications.

In one preferred embodiment of this aspect of the invention, a pharmaceutical agent is selected from the group of agents that act to decrease NMDA receptor function whether as non-competitive antagonists, ion channel blockers, or modulators of NMDA receptor function. These include, in a non-limiting fashion, memantine, dextromethorphan, and dextrorphan, a derivative of dextromethorphan with known NMDA antagonism and acceptable toxicity for human administration. One of ordinary skill in the art will recognize that the above embodiments include congeners and derivatives of memantine, dextromethorphan and dextrorphan with similar pharmacodynamic actions on glutamate transmission, and pro-drugs that are metabolized in the liver, blood, or brain to yield related compounds with similar pharmacodynamic actions on glutamate transmission. In yet another preferred embodiment, a pharmaceutical agent is selected from the group of agents that have the ability to reduce glutamate-produced excitatory post-synaptic potentials in striatal cells, (including memantine, dextromethorphan and the range of similar compounds and pro-drugs described previously). In other preferred embodiments, a combination of two or more pharmaceutical agents is selected such that the combination acts concurrently to attenuate NMDA-type glutamate transmission (e.g., by non-competitive inhibition, by indirect or modulatory effects on NMDA receptors, or by a combination or sequence of actions). A fifth embodiment is to combine such compounds or mixtures of compounds with a similar non-competitive NMDA-receptor blocking agent described in detail below. The combinations may be either mixtures, covalently-bound moieties with combined action, or pro-drugs metabolized in the blood, liver, or brain to release each member of the combination.

Risk factors for TD include advanced age, diabetes, alcoholism and a primary psychiatric diagnosis of a mood disorder rather than schizophrenia. Each of these risk factors is also associated with a high prevalence of magnesium deficiency (Durlach, et al., *Magnes Res*, March, 1998; G amez et al., *Sci. Total. Environ.*, Sep. 15, 203(3):245–51 1997; Gullestad et al., *J Am Coll Nutr*, February, 13:45–50, 1994; De Leeuw et al,. *Magnes. Res.*, June, 10:135–41, 1997; Lipski et al, *Age Ageing*, July, 22:244–55, 1993; Martin et al., *J. Trace. Elem. Electrolytes Health Dis*, September, 5:203–11, 1991; Shane et al., *Magnes. Trace. Elem.*, 10:263–8, 1991–1992; Zorbas et al., *Biol. Trace. Elem. Res.*, July–August, 58:103–16, 1997). Because people that fit the profile for being at risk for developing TD have an increased risk of magnesium deficiency, I have hypothesized that magnesium deficiency (per se) is also a risk factor for tardive dyskinesia and other movement disorders. Therefore, I further assert that magnesium supplementation can potentiate the action of other treatments, for example treatment with memantine or dextromethorphan.

Case Report 3 demonstrates that magnesium administration in combination with acamprosate and memantine augments the therapeutic action of memantine and acamprosate. Case Report 5 demonstrates that magnesium administration in combination with memantine augments the therapeutic action of memantine alone for treatment of simple tics. Thus, I propose that magnesium will augment treatment when used in combination with memantine or dextromethorphan alone for treatment of tics and Tourette's as it does when used in combination with acamprosate, given the common physiological actions of these compounds. Further support for this hypothesis is the fact that tics and Tourette's, like the tardive movement disorders, are temporarily suppressed by neuroleptics.

Magnesium supplementation can be beneficial whether or not the individual treated shows clinical signs of magnesium deficiency. (See Case Reports 3 and 4 and co-pending Patent application Ser. No. 09/193,892, filed Nov. 18, 1998 entitled "Methods of Treating Tardive Dyskinesia and Other Movement Disorders"., for full details. These cases demonstrate that patients whose tardive dyskinesia, which had improved with administration of NMDA receptor antagonists, further improved with the addition of magnesium).

In preferred embodiments of the present invention, magnesium is used to augment the efficacy of memantine, dextromethorphan, or other agents with similar effects upon NMDA-glutamate neurotransmission, in the treatment of movement disorders (e.g., tardive dyskinesia, tardive dystonia, and idiopathic focal dystonias, particularly blepharospasm).

According to the present invention magnesium supplementation will augment the therapeutic effects of other NMDA-type receptor antagonists and down-regulators. In one preferred embodiment, magnesium is administered with memantine to treat TD and other movement disorders resulting from neuroleptic drug use, as well as various focal dystonias. Also according to preferred embodiments of the present invention, magnesium is administered with memantine to treat tics, Tourette's and other tic related disorders. In another embodiment, magnesium is administered with dextromethorphan and memantine to treat TD, tics, Tourettes and other movement disorders resulting from neuroleptic drug use, as well as various focal dystonias. In one final embodiment, magnesium is administered with both memantine and dextromethorphan for treatment of movement disorders.

It will be recognized by those skilled in the art that all conditions for which memantine and dextromethorphan are effective treatments, derivatives and congeners of memantine and dextromethorphan that have similar effects on NMDA-glutamate neurotransmission will also be effective treatments. In one non-limiting example, a pill containing the appropriate dose of memantine together with the appropriate dose of magnesium may be formulated and administered to a patient with a movement disorder. Alternatively, a pill containing the appropriate dose of dextromethorphan together with the appropriate dose of magnesium may be formulated and administered to a patient with a movement disorder. One may also combine appropriate doses of memantine, dextromethorphan and magnesium in a single pill for administration to a patient for treatment of a movement disorder. In another preferred embodiment, an agent that has NMDA antagonist activity is combined with the appropriate dose of magnesium in a pill. In other preferred embodiments, an NMDA antagonist is combined with a dopamine agonist and an appropriate dose of magnesium in the form of a pill. One of ordinary skill in the art will recognize that the composition of administration is not limited to a pill, but can also be a syrup, an elixir, a liquid, a tablet, a time-release capsule, an aerosol or a transdermal patch.

The ratio of memantine and/or dextromethorphan to magnesium can be varied to optimize the therapeutic synergy of the two ingredients. Typically a combination of 5–10 mg of memantine and 250–300 mg of magnesium is administered three times per day to a patient with a movement disorder. This dosage of magnesium is below the pharmacologic doses used for neuroprotection or treatment of eclampsia. The recommended administration regime for dextromethorphan is four times per day at a dose of 30–60 mg with 250–300 mg of magnesium for treatment of movement disorders. One of ordinary skill in the art may experiment with different variations in individual response and intestinal absorption to find the optional ratio of memantine or dextromethorphan to magnesium. One of ordinary skill in the art will also recognize that optimal doses may vary if magnesium is administered with dextromethorphan and memantine simultaneously. (Because magnesium is excreted by the kidney, the dose of magnesium would we much lower in patients with renal insufficiency in addition to their movement disorder.)

Memantine, dextromethorphan and magnesium all have been advanced as neuroprotective agents, particularly in models of neuronal injury mediated by NMDA-type glutamate receptors (Representative citations for memantine: (Wenk G L, et al. *Behav Brain Res*, 83:129–33, 1997February; Kornhuber J et al.: *J Neural Transm Suppl*, 43:91–104, 1994;Weller M et al.: *Eur J Pharmacol*, 248:303–12, Dec. 1, 1993; Krieglstein J et al. *Neuropharmacology*, 35:1737–42, 1996). Representative citations for dextromethorphan: (Duhaime A C; et al. *J Neurotrauma*, 13:79–84, 1996 February; Steinberg G K et al. *Neurol Res*, 15:174–80, 1993 June; Britton P et al.: *Life Sci*, 60:1729–40, 1997). Representative citations for magnesium: Ema et al., *Alcohol, February*, 15;95–103, 1998; Greensmith et al., *Neuroscience, October*, 68:807–12, 1995; Heath et al., *J. Neurotrauma*, March, 15:183–9, 1998; Hoane et al., *Brain. Res. Bull.*, 45:45–51, 1998; Muir et al., *Magnes. Res.*, March, 11:43–56, 1998; Vanicky et al., *Brain. Res.*, April, 789:347–50, 1998). However, the immediate, short-term benefits of memantine, dextromethorphan, and magnesium for tardive movement disorders cannot be due to their neuroprotective actions, since excitotoxic neuronal damage due to neuroleptics is thought to occur gradually over months to years, while the therapeutic action of the treatments advanced here is virtually immediate.

The virtually immediate benefit of magnesium to augment the effectiveness of treatments of established movement disorders cannot be based on neuroprotection. Rather, immediate and direct effects of magnesium on neural transmission, including glutamatergic transmission, must be involved. In this connection, note that the dosages of magnesium used for neuroprotection in humans usually are well above the 1.2 grams per day that was the highest dose recommended here in the treatment of movement disorders. Indeed, magnesium, administered at doses well below those used when magnesium is a single agent can increase the beneficial effects of other treatments as described herein.

One of ordinary skill in the art will recognize that the present invention is not limited to treatment with drugs that directly block NMDA-type glutamate receptors. It will be obvious to one skilled in the art that a range of derivatives and pro-drugs all should be therapeutically effective. If a drug decreases NMDA-glutamate transmission by a mechanism other than direct effects on the receptor, or if the active substance is a metabolite of a pro-drug that is administered, it lies within the scope of the presently claimed invention as long as it improves symptoms associated with TD, tardive dystonia, and other dystonias including blepharospasm, at tolerably non-toxic doses (i.e. dosages without severe side effects).

The present invention will now be illustrated by the following non-limiting examples.

Case Report 1

A 45-year old woman had long-standing TD, originally induced by seven years exposure to amoxapine, an antidepressant drug with neuroleptic effects. The patient's irregularly-rhythmic movements consisted of forced eye blinking (blepharospasm), thrusting of the tongue forward and from side to side, tongue twisting, grimacing, shoulder shrugging, and tensing of the platysma muscles of the neck. (Had the patient's symptoms not been associated with neuroleptic exposure, a subset of her movements could be characterized as the Meige syndrome of oromandibular dystonia with blepharospasm). The patient is a semi-professional musician; the dyskinetic movements were accompanied by significant occupational disability, including difficulty reading music or text and difficulty playing woodwind instruments. Much of her reading impairment was due to frequent involuntary blinking and eye closure. She had impaired attention, concentration and memory compared with her performance before the onset of TD. She had significant fatigue, and usually required rest at some point during each day. The patient was diagnosed with TD by a board-certified neurologist with extensive experience in evaluating neuroleptic-induced side effects.

The patient's dykinesia and dystonia worsened after the amoxapine was discontinued. Palliative treatment with alprazolam (an anxiolytic and GABA agonist via modulation; dosage 0.25 mg four times a day) and trihexyphenidyl (an anticholinergic antiparkinson drug that inhibits dopamine re-uptake at synapses; dosage 2 mg twice a day) was prescribed by another physician. This combination produced minimal improvement. The patient began treatment with me in the winter of 1992 and was maintained on trihexyphenidyl for an additional 18 months. Trihexyphenidyl was then discontinued without a change in her involuntary movements. During 1993, alprazolam was increased to 0.5 mg four times a day, to treat mild symptoms of anxiety; the change in dosage had no detectable effect on the patient's involuntary movements.

Treatment trials with buspirone, sertraline, verapamil, and vitamin E in 1992 either produced little benefit or were not tolerated at doses that only slightly reduced her involuntary movements. None of these drugs significantly improved the patient's everyday function, i.e., her performance at reading text or music, her stamina or her ability to concentrate. The first drug that provided significant and sustained benefits was nimodipine, a blocker of L-type calcium channels, that indirectly reduces dopaminergic activity (Bonci et al; *J. Neurosci.*, Sep. 1, 18(17):6693–703 1998)

Beginning in 1993, nimodipine was-administered at a dosage of 30 mg four times a day. Initially, her other medications were maintained unchanged. This regime reduced the patient's involuntary movements by about 50%. Unfortunately, the patient experienced adverse effects, including dizziness, lightheadedness, and palpitations. Also, she had no symptomatic improvement in cognitive function. There was a meaningful improvement in her ability to read and to play music. However, even with this improvement, she could read text or music for no more than 30 minutes at a time, before fatigue or blepharospasm prevented her from continuing.

In 1995, memantine came to my attention as a relatively non-toxic NMDA receptor antagonist. In view of my hypothesis about the pathophysiology of tardive dyskinesia, I thought that memantine might be beneficial in its treatment. Nimodipine was discontinued, and the patient was begun on memantine at a dosage of 10 mg twice a day. The involuntary movements of the patient's TD were reduced within 24 hours of administration of memantine, to a substantially greater degree than had been observed with nimodipine. Adverse effects included a sense of mild intoxication. Adjustments to the therapeutic regime were made such that the drug was reduced to 5 mg three times a day, with the result that the therapeutic benefits were maintained without perceptible side effects. In addition, the patient reported improved energy, attention, and concentration.

Administration of a NMDA-receptor blocker such as memantine was found to be effective in reducing the abnormal movements associated with TD, while producing a demonstrable improvement in cognitive function. The effectiveness of the method of the invention for reducing the movements of TD is documented in Table 1, in which severity of the movement disorder is assessed while the patient is both on and off the drug.

TABLE 1

REACTION TIME, PSYCHOMOTOR SPEED, & MOTOR FUNCTIONING
FOR DRUG I (MEMANTINE) AND DRUG II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| Simple Reaction Time[a] | | | | | |
| 1500 Green | NA | 212 msec | 332 msec | 261 msec | 234 msec |
| 1500 Red | NA | 224 msec | 276 msec | 264 msec | 241 msec |
| 500 Green | NA | 284 msec | 343 msec | 286 msec | 272 msec |
| 500 Red | NA | 266 msec | 382 msec | 272 msec | 237 msec |
| Choice Reaction Time[a] | | | | | |
| 1500 Green | NA | 365 msec | 542 msec | 408 msec | 442 msec |
| 1500 Red | NA | 422 msec | 643 msec | 379 msec | 435 msec |
| 500 Green | NA | 362 msec | 603 msec | 382 msec | 425 msec |
| 500 Red | NA | 421 msec | 557 msec | 426 msec | 413 msec |
| PASAT[a] | | | | | |
| 2.4 sec ISI errors | 17/49 | 13/49 | 15/49 | 4/49 | 0/49 |
| 2.0 sec ISI errors | 17/49 | 17/49 | 21/49 | 1/49 | 1/49 |
| 1.6 sec ISI errors | 11/49 | 21/49 | 22/49 | 11/49 | 4/49 |
| 1.2 sec ISI errors | 17/49 | 28/49 | 25/49 | 13/49 | 11/49 |
| Digit Symbol[b] | NA | 34 | 20 | NA | NA |
| Trails A | | | | | |
| Seconds[a] | 25" | 28" | NA | 20" | 16" |
| Errors[a] | 1 | 0 | NA | 0 | 0 |
| Motor Functions | | | | | |
| Grooved Functions sec.[a] DH = right | DH = 68" NDH = 82" | DH = 71" NDH = 70" | NA | DH = 61" NDH = 70" | DH = 59" NDH = 76" |
| Finger Tapping[b] | DH = 58.8 NDH = 41.6 | DH = 59.3 NDH = 48.5 | NA | NA | NA |
| Grip Strength[b] | NA | DH = 17.7 NDH = 21.7 | NA | NA | NA |

Subjectively, the patient reported that her everyday function was improved to a greater extent during treatment with memantine than that experienced during treatment with nimodipine. She was able to read or to play her instrument for longer periods with less of a need for rest during the day. Objectively, her cognitive functioning, including attention span, concentration span and memory improved as indicated by neuropsychological testing.

Discontinuation of memantine resulted in obviously increased dyskinesia within 24 hours, to the point that the movements interfered with reading and musical activities, and caused the patient subjective distress. After re-starting memantine, involuntary movements were reduced to their previous on-treatment level within 24 hours.

The patient's excellent response to memantine supported my hypothesis that NMDA-receptor blockers might be helpful in tardive dyskinesia. To further that hypothesis, the patient was treated with dextromethorphan, an NMDA-receptor blocker thought to act at a different site on the NMDA receptor than that observed with memantine. Moreover, dextromethorphan is not a dopamine agonist like memantine or amantadine. Memantine was discontinued and the patient was started on dextromethorphan, 30 mg four times a day. Within 24 hours, the patient's dyskinetic involuntary movements were reduced to the levels seen while the patient was on memantine. However, the patient felt sedated, and felt that her attention span was shorter and her concentration worse than that experienced while on memantine.

Administration of dextromethorphan was continued for one week and reduction of the involuntary movements continued throughout this period. Increased dyskinesia was seen shortly after discontinuation of dextromethorphan administration. Again, memantine was administered, with the result that the dyskinetic movements were reduced to the same extent as during the previous administration of memantine.

Summary

This example demonstrates that efficacious treatments for TD include memantine and dextromethorphan, in an individual with prominent blepharospasm with facial and cervical dystonia (tardive Meige syndrome).

Case Report 2

A corresponding physician the United Kingdom recently reported to me on the treatment of a 47-year old woman with chronic schizophrenia and severe tardive dyskinesia. As in Case 1, the patient's involuntary movements included severe blepharospasm. In addition, she had involuntary rhythmic peri-oral movements, and chorea-like movements of both hands.

The patient had developed symptoms of paranoid schizophrenia in 1991, at age 40. The symptoms of psychosis included auditory hallucinations, bizarre delusions, and persecutory fears. She was started on oral haloperidol as an outpatient in July 1992 and had an acute dystonic reaction to the drug. She was subsequently hospitalized and stabilized on fluphenthixol decanoate, a depot neuroleptic given by intramuscular injections. Symptoms of TD developed in November, 1994, after 28 months of neuroleptic therapy. Switching the patient to an atypical neuroleptic, olanzapine or risperidone, did not eliminate her TD. Beginning in October 1997 the patient was treated for her schizophrenia with 2 mg of risperidone alone. On this modest dose of an atypical neuroleptic, she had severe symptoms of TD for which she eagerly sought treatment.

Memantine was started on Nov. 28, 1997 at a dose of 5 mg per day, increased after 7 days to 5 mg twice a day, and after another 7 days to 5 mg three times a day. After the first two weeks of memantine treatment (an on 5 mg twice a day) there was marked improvement in blepharospasm, though the movements started to return just before the second dose of the day was due. Two weeks later, on 5 mg three times a day, improvement was more sustained, with virtually no involuntary movements noted at the peak of a given dose of memantine, and only mild movements noted when a dose was due. Further dosage increases were attempted to completely abolish the involuntary movements. The maximum dose attainable without side effects was 10 mg twice a day; above that level the patient had complaints of dizziness. That dose of memantine was maintained through May of 1997. At that point, after 6 months of treatment with memantine, the patient had no blepharospasm or limb chorea, and only mild peri-oral movements. Benefit persisted through May 1998, when the patient discontinued memantine in favor of acamprosate (another drug that decreases NMDA glutamate neurotransmission).

Summary

Memantine can alleviate the involuntary movements of TD in patients with chronic schizophrenia who continue to require neuroleptic therapy. In particular, memantine can relieve severe neuroleptic-induced blepharospasm. The response of drug-induced blepharospasm to memantine suggests that memantine will be helpful in the treatment of idiopathic (spontaneous) blepharospasm. By extension, can be expected to be useful in the treatment of other focal dystonias.

Case Report 3

A 79-year old woman had long-standing TD following decades of treatment with the neuroleptic drug perphenazine. Her involuntary movements comprised bilateral chorea of the upper extremities, plus writhing of the tongue and tongue-biting. Both of the latter movements led to a very sore tongue. In addition, the patient experienced impairment of her short-term memory, which was attributed primarily to cerebrovascular disease.

Following treatment with memantine the patient's voluntary movements improved, but continued at a mild-to-moderate level. She also continued to have a sore tongue. Her cognitive symptoms did not improve. In addition to memantine, the patient regularly took antiepileptic drugs (gabapentin and lamotrigine), antiplatelet agents (aspirin and ticlopidine), as well as medications for hypertension, glaucoma and gastrointestinal symptoms (isosorbide mononitrate, metoprolol, timolol eye drops and olsalazine). These various drugs did not affect the patient's involuntary movements or cognitive symptoms; there was no noticeable change in either one at the time that each of the above-mentioned drugs was instituted.

The patient was placed on a treatment regime that included administration of 666 mg of acamprosate, three times daily. In this case, acamprosate was added to the patient's regimen, which continued to include memantine. Once the patient began taking acamprosate, her chorea and tongue-biting stopped completely, and the writhing movements of the tongue diminished substantially. Subjectively, the patient's memory improved to the extent that her long-term bridge partner stated that patient was noticeably better at remembering cards during the play of duplicate bridge. Despite past evidence from formal testing that the patient had impaired short-term memory, she performed normally on a two-sentence memory task, which involved testing the patient's recall ability using two sentences containing 13 separate details. On the two-sentence memory task, within three attempts the patient was able to recall 9 details and, using a multiple choice format, was able to recall a total of 11 details. Recall of 9 details on the third attempt would be normal for a middle-aged adult, let alone one in her 80s at the time of testing.

After a full year on memantine and acamprosate, the memantine was discontinued, with little change in the patient's symptoms. On acamprosate 666 mg three times a day, persistent symptoms included mild choreatic movements on the hands, mild involuntary movements of the tongue and jaw, and soreness of the tongue disproportionate to the visible involuntary movements.

Magnesium oxide, 250 mg three times a day, was added, each dose being taken together with the acamprosate. The movements and the tongue soreness improved further. The effect was definite: movements worsened when magnesium oxide was stopped and improved when it was restarted. After a month on magnesium, the dosage of acamprosate was increased to 666 mg four times a day, with 250 mg of magnesium oxide given together with each dose. On this regimen, the tongue movements and tongue soreness were completely eliminated. The only residual sign of TD was a mild degree of involuntary movement of the hands.

Summary

Magnesium and acamprosate are efficacious treatments of tardive dyskinesia when administered alone. More specifically, Case Report 3 demonstrates that acamprosate can improve both the involuntary movements associated with TD as well as the associated cognitive impairment, in a patient in whom memantine improves involuntary movements but not cognition. Furthermore magnesium, when administered with acamprosate and memantine can augment the efficacy of acamprosate in the treatment o TD. In this case, the combination of acamprosate memantine and magnesium was efficacious at an magnesium:acamprosate ratio or 1:2.66. It is logical to infer that treatment with memantine and magnesium would be better than memantine treatment alone.

Case Report 4

A 46 year old man had simple tic of the neck that involved forceful extension and rotation of the neck to the right. The tic had started in the context of therapy of depression with dextroamphetamine and pramipexole, a dopamine agonist drug. The tic occurred from 20–50 times per hour, with greater frequency when he was tired or under stress.

He was initially treated with 666 mg of acamprosate three times a day. Within 24 hours after the start of acamprosate therapy, the frequency and severity of the tic decreased dramatically, to a rate of less than 5 per hour. The patient often was free of tics completely for 2 to 3 hours after each dose of acamprosate, after which time the tic would very gradually return. The dose was then raised to 666 mg four times a day. On this dose, rates of more than 5 per hour occurred only under unusually stressful circumstances, and there were frequent tic-free periods of 4 hours or more. If acamprosate was omitted for a full day, the frequency of tics rapidly increased, to over 10 an hour. On a second day without acamprosate, the rate of tics was again over 20 per hour.

He then added chelated magnesium, at a dosage of 300 mg of elemental magnesium 3 times a day. With magnesium supplementation, the average tic frequency dropped to 6 hour or less. When 666 mg of acamprosate was given three times a day was given together with magnesium 300 mg three times a day, the usual tic-free period after each acamprosate dose increased from approximately 3 hours to approximately 5 hours.

Summary

Acamprosate is efficacious in the treatment of a simple tic. The efficacy of acamprosate is enhanced by concurrent administration of magnesium. In this case, a good effect was obtained at a magnesium:acamprosate ratio of 1:2.22. By extension, acamprosate should be efficacious in the treatment of multiple tics and Gilles de la Tourette syndrome. By extension, it is logical to propose that the effect of memantine will also be enhanced by coadministration of magnesium, since acamprosate and memantine act alone similar biochemical pathways.

Case Report 5

A 46 year old man had simple tic of the neck that involved forceful extension and rotation of the neck to the right. The tic had started in the context of therapy of depression with dextroamphetamine and pramipexole, a dopamine agonist drug. The tic occurred from 20–50 times per hour, with greater frequency when he was tired or under stress.

He was initially treated with 666 mg of acamprosate three times a day. Within 24 hours after the start of acamprosate therapy, the frequency and severity of the tic decreased dramatically, to a rate of less than 5 per hour. The patient often was free of tics completely for 2 to 3 hours after each dose of acamprosate, after which time the tic would very gradually return. The dose was then raised to 666 mg four times a day. On this dose, rates of more than 5 per hour occurred only under unusually stressful circumstances, and there were frequent tic-free periods of 4 hours or more. If acamprosate was omitted for a full day, the frequency of tics rapidly increased, to over 10 an hour. On a second day without acamprosate, the rate of tics was again over 20 per hour.

He then added chelated magnesium, at a dosage of 300 mg of elemental magnesium 3 times a day. With magnesium supplementation, the average tic frequency dropped to 6 hour or less. When 666 mg of acamprosate was given three times a day was given together with magnesium 300 mg three times a day, the usual tic-free period after each acamprosate dose increased from approximately 3 hours to approximately 5 hours.

Acamprosate treatment was later replaced with memantine, 10 mg twice a day, for two doses with supplemental magnesium (300 mg). Memantine with magnesium resulted in a tic-free interval of 6–7 hours. Next, the memantine was administered, 10 mg twice a day for two doses without supplemental magnesium. Administration of memantine without magnesium produced a tic-free period of only 4–5 hours beginning about 30 minutes after a dose.

Summary

Acamprosate is efficacious in the treatment of a simple tic. The efficacy of acamprosate is enhanced by concurrent administration of magnesium. In this case, a good effect was obtained at a magnesium:acamprosate ratio of 1:2.22. By extension, acamprosate should be efficacious in the treatment of multiple tics and Gilles de la Tourette syndrome. Furthermore, this study demonstrates that memantine is an efficacious treatment for tics and the efficacy of memantine is enhanced by concurrent administration of magnesium in a manner similar to that of acamprosate.

Discussion

The patients discussed in the two cases presented all exhibited a marked decrease in the frequency and severity of dyskinetic movements. Relief of symptoms began within 48 hours of administration of treatment, and, if a patient discontinued treatment, symptoms returned immediately. This evidence supports my novel hypothesis that pharmacological agents such as memantine and dextromethorphan, or derivatives with similar pharmacodynamic actions, will be helpful in the treatment tardive movement disorders, including TD, tardive dystonia, tics and Tourette's. In particular, Case Reports 1 and 2 demonstrate that memantine can relieve blepharospasm and Meige syndrome associated with more extensive tardive movement disorders. By extension, I predict that memantine (with and without magnesium) and related agents will also be successful treatments for idiopathic blepharospasm and Meige syndrome, as well as other focal dystonias such as spasmodic torticollis, writer's cramp and other occupational dystonias.

Moreover, I have presented evidence elsewhere (See co-pending application Ser. No. 09/193,892, filed Nov. 18, 1998, entitled "Methods of Treating Tardive Dyskinesia and Other Movement Disorders") that magnesium, an antagonist of NMDA glutamate neurotransmission via ion channel blockade, can augment the therapeutic action of other NMDA receptor antagonists on movement disorders including tardive dyskinesia and tardive dystonia. One can infer from this work, and it is herein demonstrated, that magnesium will augment the therapeutic effect of memantine and dextromethorphan for tardive movement disorders, as well as for spontaneous movement disorders that closely mimic tardive movement disorders, including without limitation blepharospasm and Meige syndrome, as well as other focal dystonias such as spasmodic torticollis, writer's cramp and other occupational dystonias.

Symptoms of the movement disorder associated with Huntington's disease, specifically dyskinetic and choreatic movements of the face and limbs, also can closely resemble symptoms of TD. Therefore, one can predict that they will be relieved, at least in part, by memantine or dextromethorphan, alone or in combination with magnesium.

Based on the foregoing, I claim the following:

1. A method of treating a human subject for involuntary movement symptoms of movement disorders selected from the group consisting of dystonia and tardive dyskinesia comprising:
    administering to said human subject an effective amount of a NMDA-receptor antagonist selected from the group consisting of memantine and derivatives and congeners thereof that have similar pharmacodynamic effects in respect to NMDA-type glutamate neurotransmission.

2. The method of claim 1 wherein the dystonia includes blepharospasm, torticollis, Meige syndrome, cervical dystonia, tardive dysphonia, focal dystonia, spasmodic torticollis, spasmodic dysphonia, writer's cramp, musician' cramp and oromandibular dystonia.

3. The method of claim 1, wherein said NMDA-receptor antagonist is available in the blood.

4. The method of claim 1, wherein said NMDA-receptor antagonist is available in the brain.

5. The method of claim 1, wherein said NMDA-receptor antagonist is a pro-drug metabolized in the body to release an active compound into the body.

6. The method of claim 5, wherein the compound released into the body is selected from the group consisting of any derivative or congener of memantine with pharmacodynamic effects on NMDA-type glutamate neurotransmission similar to those of memantine.

7. The method of claim 6, wherein said derivative or congener is a pro-drug metabolized in the liver, blood, or brain to release any derivative with similar pharmacodynamic effects on glutamate neurotransmission.

8. The method of claim 6, wherein said derivatives or congeners have a longer duration of action than memantine.

9. The method of claim 1, wherein said step of administering comprises oral administration.

10. A method for treating involuntary movement symptoms of a human patient for involuntary movement symptoms of movement disorders selected from the group consisting of dystonia and tardive dyskinesia comprising the steps of:
    selecting a first pharmacologically active agent that acts as a NMDA-type glutamate receptor antagonist; and
    administering an effective amount of said first agent to a human patient with a movement disorder.

11. The method of claim 10 wherein the dystonia includes blepharospasm, torticollis, Meige syndrome, cervical dystonia, tardive dysphonia, focal dystonia, spasmodic torticollis, spasmodic dysphonia, writer's cramp, musician's cramp and oromandibular dystonia.

12. The method of claim 11, wherein the blepharospasm is idiopathic blepharospasm.

13. The method of claim 11, wherein the blepharospasm is induced by exposure to neuroleptics or other dopamine receptor antagonists, or is associated with a more extensive neuroleptic-induced movement disorder.

14. The method of claim 10, wherein the step of administering comprises selecting dosages of the first agent such that the administration of said first dosage reduces symptoms of said movement disorder at non-toxic dosages.

15. The method of claim 10, wherein said movement disorder comprises involuntary movements similar to those seen in tardive dyskinesia, tardive dystonia, or focal dystonias not associated with neuroleptic drug use.

16. The method of claim 10, wherein said movement disorder is associated with Huntington's disease.

17. The method of claim 10, wherein the step of selecting further comprises selecting a second pharmacologically active agent that is a noncompetitive NMDA receptor antagonist, or an ion channel blocker at channels linked to NMDA receptors.

18. The method of claim 17, wherein the step of administering further comprises administering an effective amount of said second agent in conjunction with said first agent.

19. The method of claim 17, wherein said second agent is memantine or a derivative or congener of memantine with similar pharmacodynamic effects at NMDA receptors as memantine.

20. The method of claim 17, wherein said second agent is magnesium.

21. A method of treating involuntary movement symptoms of movement disorders comprising: augmenting the therapeutic effects of memantine in human patients with movement disorders by administering to said patient an effective dose of magnesium ion.

22. A method of treating involuntary movement symptoms of movement disorders comprising: augmenting the therapeutic effects of dextromethorphan in human patients with movement disorders by administering to said patient an effective dose of magnesium ion.

23. The method of claims 21 or 22, wherein said movement disorder is selected from the group of the focal dystonias, including without limitation tics, Tourette's, blepharospasm, Meige syndrome, spasmodic torticollis, spasmodic dysphonia, writer's cramp, musician's cramp, and other occupational dystonias.

24. A method for treating involuntary movement symptoms of a movement disorder comprising: administering to a human patient in combination, a single composition at an effective dose,
    (i) an NMDA receptor antagonist; and
    (ii) magnesium ion.

25. The method of claim 24, wherein the NMDA antagonist is selected from the group consisting of memantine, dextromethorphan, and derivatives and congeners thereof with similar pharmacodynamic effects upon glutamate neurotransmission as memantine or dextromethorphan.

26. The method of claim 24, wherein said NMDA antagonist is available in the blood.

27. The method of claim 24, wherein said NMDA antagonist is available in the brain.

28. The method of claim 25, wherein said derivative or congener is a pro-drug metabolized in the liver, blood, or brain to release any derivative with similar pharmacodynamic effects on glutamate neurotransmission.

29. The method of claim 25, wherein said derivative or congener has a longer effective duration of action than memantine or dextromethorphan, elimination half-life or by being absorbed over a longer period.

30. The method of claim 24, wherein the composition is used to treat blepharospasm or Meige syndrome.

31. The method of claim 24, wherein the composition is used to treat other focal dystonias, including without limitation spasmodic torticollis, spastic dysphonia, writer's cramp, musician's cramp, and other occupational dystonias.

32. The method of claim 24, wherein the composition administered to a patient is administered in the form of a pill, a syrup, an elixir, a liquid, a tablet, a time-release capsule, an aerosol or a transdermal patch.

33. A composition for treating movement disorders in a human subject comprising:

one or more agents that decrease NMDA-glutamate neurotransmission; and an effective amount of magnesium ion.

34. The composition of claim 33, wherein said composition is a compound.

35. The composition of claim 33, wherein said composition is a mixture.

36. The composition of claim 33, wherein the magnesium ion is in the form of a magnesium salt.

37. The composition of claim 33, wherein the magnesium ion is in the form of a chelate.

38. The composition of claim 33, wherein said composition is available in the blood.

39. The composition of claim 33, wherein said composition is available in the brain.

40. The composition of claim 33, wherein the composition that decreases NMDA-glutamate neurotransmission is selected from the group consisting of memantine, dextromethorphan, and derivatives and congeners thereof with similar pharmacodynamic effects upon glutamate neurotransmission as memantine.

41. The composition of claim 38, wherein said derivative or congener is a pro-drug metabolized in the liver, blood, or brain to release any derivative with similar pharmacodynamic effects on glutamate neurotransmission as memantine.

42. The composition of claim 38, wherein said derivative or congener has a longer effective duration of action than memantine.

43. The composition of claim 38, wherein said derivative or congener is absorbed over a longer period of time than memantine.

44. The composition of claim 38, wherein the derivative or congener has a longer elimination half life than memantine.

45. The composition of claim 33, wherein the composition is used to treat blepharospasm or Meige syndrome.

46. The composition of claim 33, wherein the composition is used to treat focal dystonias.

47. The composition of claim 33, wherein said composition is delivered in the form of delivery agent comprising a pill, a syrup, an elixir, a liquid, a tablet, a time-release capsule an aerosol or a transdermal patch.

48. A composition for the treatment of involuntary movement symptoms of movement disorders in a human subject comprising:

(i) a effective amount of memantine (ii) an effective amount of an inorganic salt or chelate of magnesium.

49. A composition for the treatment of involuntary movement symptoms of movement disorders in a human subject comprising:

(i) an effective amount of memantine (ii) an effective amount of dextromethorphan (ii) an effective amount of an inorganic salt or chelate of magnesium.

50. The composition of claim 48, or 49, wherein the inorganic salt or chelate of magnesium comprises magnesium chloride, magnesium oxide, magnesium sulfate, and magnesium chelated with any of various amino acids.

51. The composition of claim 48, or 49, wherein said movement disorder is selected from the group consisting of, tics, Tourette's, tardive dyskinesia, tardive dystonia, and the group of focal dystonias not due to neuroleptic drug exposure, including without limitation, blepharospasm and Meige syndrome, spasmodic torticollis, spasmodic dysphonia, writer's cramp, musician's cramp, and other occupational dystonias.

52. The composition of claim 48, or 49, wherein memantine is replaced by a derivative or congener of memantine.

* * * * *

UNITED STATES PATENT AND TRADEMARK OFFICE
CERTIFICATE OF CORRECTION

PATENT NO. : 6,057,373
DATED : MAY 2, 2000
INVENTOR(S) : BARRY S. FOGEL

It is certified that error appears in the above-identified patent and that said Letters Patent is hereby corrected as shown below:

In column 1, line 10, please delete 5,868,580, and substitute the following therefor:

5,866,585

Signed and Sealed this

Seventeenth Day of April, 2001

Attest:

NICHOLAS P. GODICI

Attesting Officer     *Acting Director of the United States Patent and Trademark Office*